(12) United States Patent
Hunziker

(10) Patent No.: US 8,961,567 B2
(45) Date of Patent: Feb. 24, 2015

(54) NON-FUSION SCOLIOSIS EXPANDABLE SPINAL ROD

(75) Inventor: Markus Hunziker, Aarau (CH)

(73) Assignee: DePuy Synthes Products, LLC, Raynham, MA (US)

( * ) Notice: Subject to any disclaimer, the term of this patent is extended or adjusted under 35 U.S.C. 154(b) by 364 days.

(21) Appl. No.: 13/302,187

(22) Filed: Nov. 22, 2011

(65) Prior Publication Data
US 2012/0130428 A1     May 24, 2012

Related U.S. Application Data

(60) Provisional application No. 61/416,266, filed on Nov. 22, 2010.

(51) Int. Cl.
*A61B 17/70* (2006.01)
*A61B 1/00* (2006.01)
*A61B 17/00* (2006.01)

(52) U.S. Cl.
CPC ......... *A61B 17/7016* (2013.01); *A61B 1/00158* (2013.01); *A61B 2017/00017* (2013.01)
USPC .......................................... 606/258; 606/259

(58) Field of Classification Search
CPC ................. A61B 17/7016; A61B 1/00158
USPC ........................................ 606/258–260, 63
See application file for complete search history.

(56) References Cited

U.S. PATENT DOCUMENTS

| | | |
|---|---|---|
| 3,270,792 A | 9/1966 | Nenschotz et al. |
| 3,810,259 A | 5/1974 | Summers |
| 3,976,060 A | 8/1976 | Hildebrandt et al. |
| 4,312,336 A | 1/1982 | Danieletto et al. |
| 4,453,539 A | 6/1984 | Raftopoulos et al. |
| 4,665,736 A | 5/1987 | Yokoyama et al. |
| 4,850,821 A | 7/1989 | Sakai |
| 4,921,499 A | 5/1990 | Hoffman et al. |
| 4,926,708 A | 5/1990 | Dietrich et al. |

(Continued)

FOREIGN PATENT DOCUMENTS

| | | |
|---|---|---|
| FR | 2906453 | 4/2008 |
| WO | 9934746 | 7/1999 |

(Continued)

OTHER PUBLICATIONS

PCT Patent Application No. PCT/US2011/061767, International Search Report and Written Opinion mailed Mar. 1, 2012 (19 pages).

(Continued)

*Primary Examiner* — Ellen C Hammond
(74) *Attorney, Agent, or Firm* — Meunier Carlin & Curfman, LLC

(57) ABSTRACT

A growing rod for mounting between attachment mechanisms that are secured to anatomical structures of a patient having scoliosis. The growing rod includes an outer housing and an inner housing disposed within the outer housing. The inner housing includes a magnet assembly including a magnet having a first pole and a second pole and a gear reduction mechanism coupled to the magnet. A first rod is secured to the inner housing and a second rod is secured to the outer housing. The gear reduction mechanism reduces an output rotation of the magnet to rotate a driver that operates to move the inner housing along a longitudinal axis with respect to the outer housing.

30 Claims, 9 Drawing Sheets

(56) References Cited

U.S. PATENT DOCUMENTS

| | | |
|---|---|---|
| 4,946,459 A | 8/1990 | Bradshaw et al. |
| 4,979,672 A | 12/1990 | AbuJudom, II et al. |
| 5,013,949 A | 5/1991 | Mabe, Jr. |
| 5,035,712 A | 7/1991 | Hoffman |
| 5,074,882 A | 12/1991 | Grammont et al. |
| 5,120,135 A | 6/1992 | Ullman |
| 5,150,770 A | 9/1992 | Secci |
| 5,263,955 A | 11/1993 | Baumgart et al. |
| 5,356,411 A | 10/1994 | Spievack |
| 5,364,396 A | 11/1994 | Robinson et al. |
| 5,415,660 A | 5/1995 | Campbell et al. |
| 5,505,733 A | 4/1996 | Justin et al. |
| 5,536,269 A | 7/1996 | Spievack |
| 5,551,871 A | 9/1996 | Besselink et al. |
| 5,569,967 A | 10/1996 | Rode |
| 5,575,790 A | 11/1996 | Chen et al. |
| 5,626,579 A | 5/1997 | Muschler et al. |
| 5,626,581 A | 5/1997 | Staehlin et al. |
| 5,672,177 A | 9/1997 | Seldin |
| 5,700,263 A | 12/1997 | Schendel |
| 5,704,939 A | 1/1998 | Justin |
| 5,720,746 A | 2/1998 | Soubeiran |
| 5,762,599 A | 6/1998 | Sohn |
| 5,766,004 A | 6/1998 | Besselink et al. |
| 5,827,286 A | 10/1998 | Incavo et al. |
| 5,961,553 A | 10/1999 | Coty et al. |
| 6,033,412 A | 3/2000 | Losken et al. |
| 6,036,690 A | 3/2000 | De La Plaza Fernandez |
| 6,187,004 B1 | 2/2001 | Fearon |
| 6,245,075 B1 | 6/2001 | Betz et al. |
| 6,277,124 B1 | 8/2001 | Haag |
| 6,326,707 B1 | 12/2001 | Gummin et al. |
| 6,336,929 B1 | 1/2002 | Justin |
| 6,358,255 B1 | 3/2002 | Testa |
| 6,375,638 B2 | 4/2002 | Nason et al. |
| 6,383,185 B1 | 5/2002 | Baumgart |
| 6,417,750 B1 * | 7/2002 | Sohn ............................... 335/207 |
| 6,565,576 B1 | 5/2003 | Stauch et al. |
| 6,616,672 B1 | 9/2003 | Essiger |
| 6,673,079 B1 | 1/2004 | Kane |
| 6,684,724 B2 | 2/2004 | Narasimhiah et al. |
| 6,684,904 B2 | 2/2004 | Ito |
| 6,706,042 B2 | 3/2004 | Taylor |
| 6,716,218 B2 | 4/2004 | Holmes et al. |
| 6,730,087 B1 | 5/2004 | Butsch |
| 6,769,830 B1 | 8/2004 | Nygren |
| 6,783,530 B1 | 8/2004 | Levy |
| 6,796,984 B2 | 9/2004 | Soubeiran |
| 6,832,477 B2 | 12/2004 | Gummin et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,860,691 B2 | 3/2005 | Unsworth et al. |
| 6,918,910 B2 | 7/2005 | Smith et al. |
| 6,918,980 B2 | 7/2005 | Grabarz |
| 7,021,055 B2 | 4/2006 | Gummin et al. |
| 7,063,706 B2 | 6/2006 | Wittenstein |
| 7,135,022 B2 | 11/2006 | Kosashvili et al. |
| 7,240,677 B2 | 7/2007 | Fox |
| 7,282,052 B2 | 10/2007 | Mullaney |
| 7,297,146 B2 | 11/2007 | Braun et al. |
| 7,666,184 B2 | 2/2010 | Stauch |
| 7,862,502 B2 | 1/2011 | Pool et al. |
| 7,955,357 B2 | 6/2011 | Kiester |
| 8,043,290 B2 | 10/2011 | Harrison et al. |
| 8,043,299 B2 | 10/2011 | Conway |
| 8,057,472 B2 * | 11/2011 | Walker et al. ............ 606/57 |
| 8,137,349 B2 | 3/2012 | Soubeiran |
| 8,142,454 B2 | 3/2012 | Harrison et al. |
| 8,197,490 B2 | 6/2012 | Pool et al. |
| 8,343,192 B2 | 1/2013 | Kiester |
| 8,419,734 B2 | 4/2013 | Walker et al. |
| 8,439,915 B2 | 5/2013 | Harrison et al. |
| 8,525,063 B2 | 9/2013 | Yamazaki |
| 2003/0032958 A1 | 2/2003 | Soubeiran |
| 2004/0030395 A1 | 2/2004 | Blunn et al. |
| 2004/0059331 A1 | 3/2004 | Mullaney |
| 2004/0193266 A1 | 9/2004 | Meyer |
| 2005/0234448 A1 | 10/2005 | McCarthy |
| 2005/0246034 A1 | 11/2005 | Soubeiran |
| 2005/0251109 A1 | 11/2005 | Soubeiran |
| 2005/0261779 A1 | 11/2005 | Meyer |
| 2006/0009767 A1 | 1/2006 | Kiester |
| 2006/0047282 A1 | 3/2006 | Gordon |
| 2006/0074448 A1 | 4/2006 | Harrison et al. |
| 2006/0079897 A1 | 4/2006 | Harrison et al. |
| 2006/0271107 A1 | 11/2006 | Harrison et al. |
| 2007/0010814 A1 | 1/2007 | Stauch |
| 2007/0015622 A1 | 1/2007 | Stauch |
| 2007/0073098 A1 | 3/2007 | Lenker et al. |
| 2007/0185374 A1 | 8/2007 | Kick et al. |
| 2007/0265646 A1 | 11/2007 | McCoy et al. |
| 2007/0270803 A1 | 11/2007 | Giger et al. |
| 2007/0276378 A1 | 11/2007 | Harrison et al. |
| 2007/0282338 A1 | 12/2007 | Mullaney |
| 2008/0097188 A1 | 4/2008 | Pool et al. |
| 2008/0097249 A1 | 4/2008 | Pool et al. |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0172072 A1 | 7/2008 | Pool et al. |
| 2009/0062825 A1 | 3/2009 | Pool et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0204154 A1 | 8/2009 | Kiester |
| 2009/0254088 A1 | 10/2009 | Soubeiran |
| 2010/0049204 A1 | 2/2010 | Soubeiran |
| 2010/0094302 A1 | 4/2010 | Pool et al. |
| 2010/0094303 A1 | 4/2010 | Chang et al. |
| 2010/0094304 A1 | 4/2010 | Pool |
| 2010/0094305 A1 | 4/2010 | Chang et al. |
| 2010/0094306 A1 | 4/2010 | Chang et al. |
| 2010/0121323 A1 | 5/2010 | Pool et al. |
| 2010/0217271 A1 | 8/2010 | Pool et al. |
| 2010/0280519 A1 | 11/2010 | Soubeiran |
| 2010/0280551 A1 | 11/2010 | Pool et al. |
| 2011/0060336 A1 | 3/2011 | Pool et al. |
| 2011/0238126 A1 | 9/2011 | Soubeiran |
| 2012/0004494 A1 | 1/2012 | Payne et al. |
| 2012/0035656 A1 | 2/2012 | Pool et al. |
| 2012/0035661 A1 | 2/2012 | Pool et al. |
| 2012/0157996 A1 | 6/2012 | Walker et al. |
| 2013/0296859 A1 | 11/2013 | Walker et al. |

FOREIGN PATENT DOCUMENTS

| | | |
|---|---|---|
| WO | 9951160 | 10/1999 |
| WO | 0033752 | 6/2000 |
| WO | 2008109300 | 9/2008 |
| WO | 2009058546 | 5/2009 |
| WO | WO 2010/052465 A1 * | 5/2010 |

OTHER PUBLICATIONS

U.S. Appl. No. 14/056,441, filed Oct. 17, 2013.

International Preliminary Report on Patentability and Written Opinion, dated Jun. 5, 2012, in connection with International Application No. PCT/US2010/058528.

International Search Report, dated Feb. 17, 2011, in connection with International Application No. PCT/US2010/058528.

International Preliminary Report on Patentability and Written Opinion, dated May 22, 2013, in connection with International Application No. PCT/US2011/061767.

Campbell et al., "Expansion Thoracoplasty: The Surgical Technique of Opening-Wedge Thoracostomy," JBJS, vol. 85-A, pp. 409-420, Mar. 2003.

Campbell et al., "Growth of the Thoracic Spine in Congenital Scoliosis After Expansion Thoracoplasty," JBJS, vol. 85-A, pp. 409-420, Mar. 2003.

Campbell et al., "The Effect of Opening Wedge Thoracostomy on Thoracic Insufficiency Syndrome Syndrome Associated with Fused

(56) References Cited

OTHER PUBLICATIONS

Ribs and Congenital Scoliosis," JBJS, vol. 86-A, pp. 1659-1674, Aug. 2004.
Campbell et al., "Thoracic Insufficiency Syndrome and Exotic Scoliosis," JBJS, vol. 89-A, Supp. 1, pp. 108-122, 2007.
Cunningham et al., "Fusionless Scoliosis Surgery," Curr Opin Pediatr, Lippincott Williams & Wilkins, vol. 17, pp. 48-53, 2005.
Deacon et al., "Idiopathic Scoliosis in Three Dimensions: A Radiographic and Morphometric Analysis," The Journal of Bone and Joint Surgery, British Editorial Society of Bone and Joint Surgery, vol. 66-B, pp. 509-512, Aug. 1984.
Edeland et al., "Instrumentation for Distraction by Limited Surgery in Scoliosis Treatment," Journal of Biomedical Engineering, vol. 3, pp. 143-146, Apr. 1981.
Emans et al., "The Treatment of Spine and Chest Wall Deformities with Fused Ribs by Expansion Thoracostomy and Insertion of Vertical Expandable Prosthetic Titanium Rib," Spine, Lippincott Williams & Wilkins, Inc., vol. 30, No. 17S, pp. 558-568, 2005.
Grass et al., "Intermittent Distracting Rod for Correction of High Neurologic Risk Congenital Scoliosis," Spine, vol. 22, No. 16, pp. 1922-1927, 1997.
Hefti, "Idiopathic Scoliosis," Pediatric Orthopedics in Practice, Springer Berlin Heidelberg, pp. 72-94, 2007.
Keynan et al., "Radiographic Measurement Parameters in Thoracolumbar Fractures: A Systematic Review and Consensus Statement of the Spine Trauma Study Group," Spine, Lippincott Williams & Wilkins, Inc., vol. 31, No. 5, pp. E156-E163, 2006.
Klemme et al., "Spinal Instrumentation Without Fusion for Progressive Scoliosis in Young Children," Journal of Pediatric Orthopaedics, Lippincott-Raven Publisher, vol. 17, pp. 734-742, 1997.
Stokes et al., "Three-Dimensional Spinal Curvature in Idiopathic Scoliosis," Journal of Orthopaedic Research, Orthopeadic Research Society, Raven Press, NY, vol. 5, pp. 102-113, 1987.
Takaso et al., "New Remote-Controlled-Growing-Rod Spinal Instrumentation Possibly Applicable for Scoliosis in Young Children," Journal of Orthopedic Science, vol. 3, pp. 336-340, 1998.
Wenger, "Spine Jack Operation in the Correction of Scoliotic Deformity," Archives of Surgery, vol. 83, pp. 901-910, 1961.

* cited by examiner

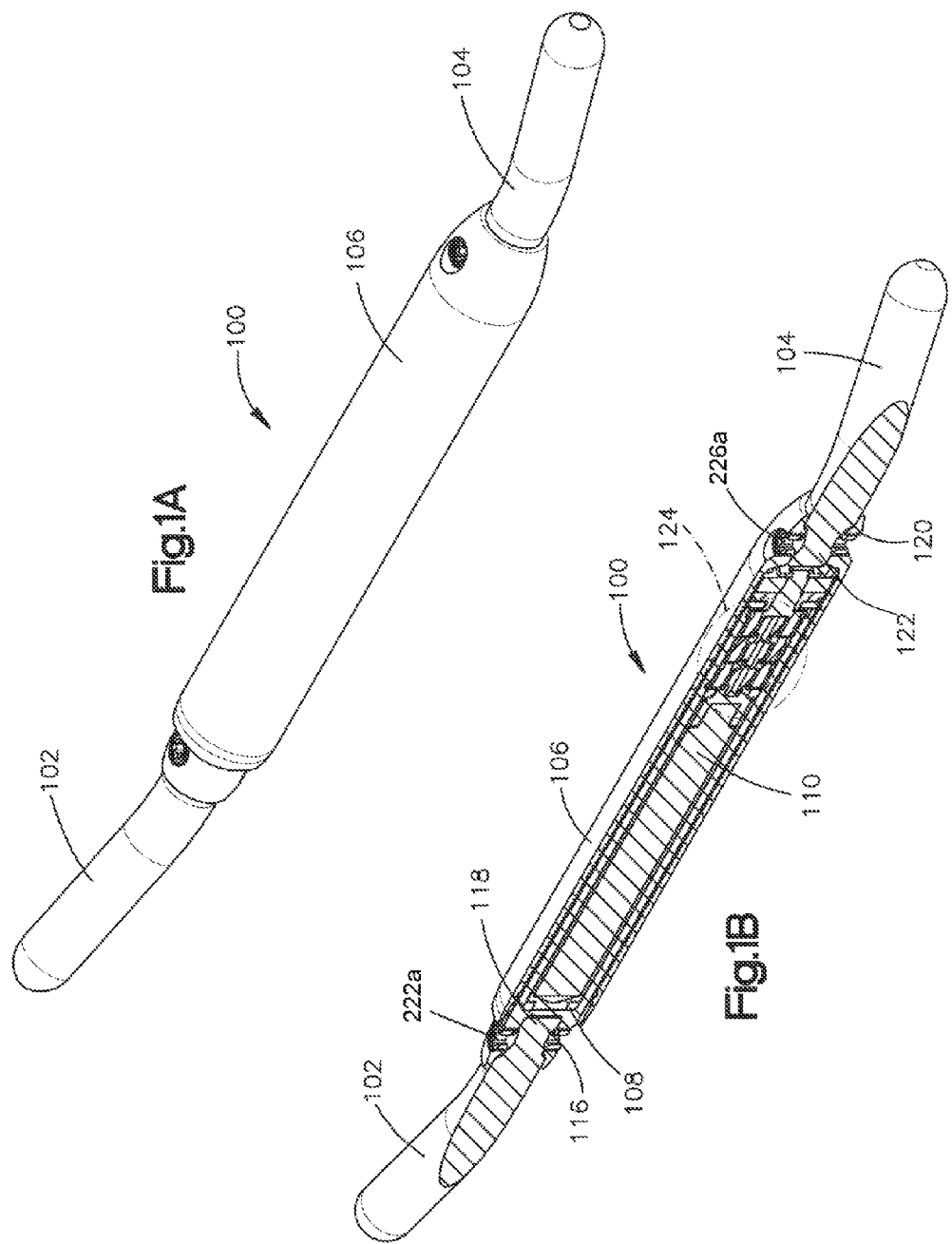

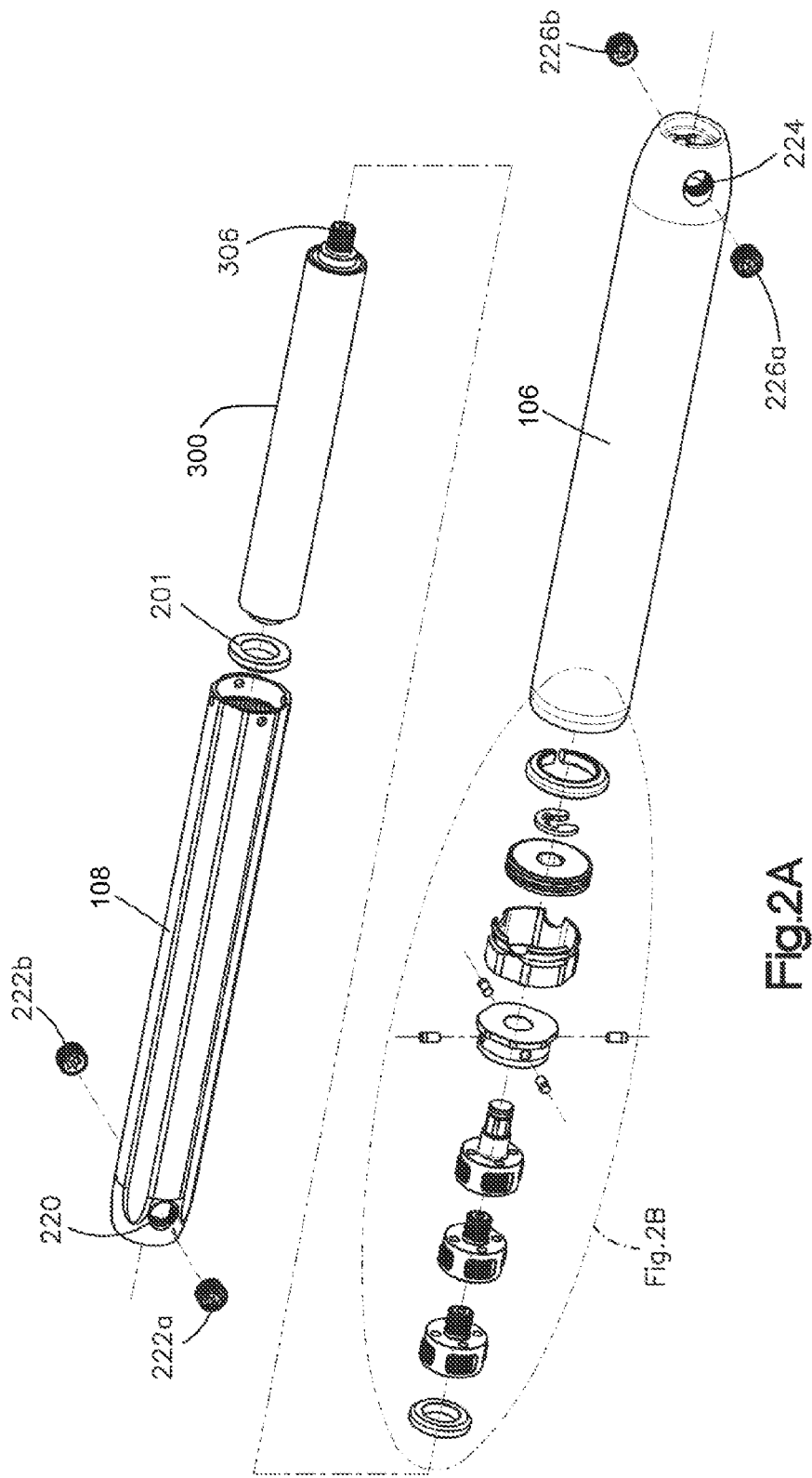

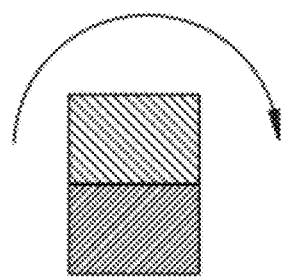
Fig.4A
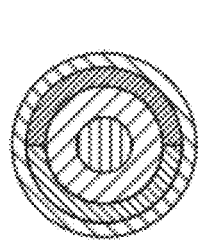　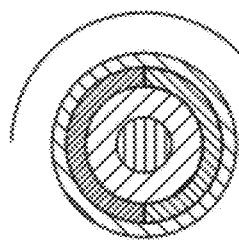　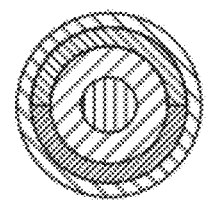
Fig.4B　　　Fig.4C　　　Fig.4D
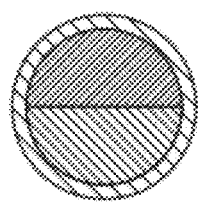　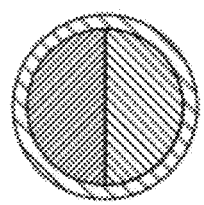　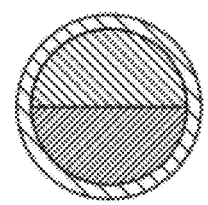
Fig.4E　　　Fig.4F　　　Fig.4G
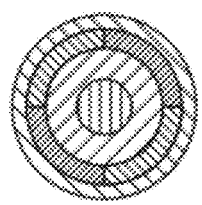　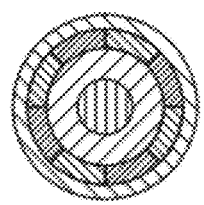
Fig.4H　　　Fig.4I

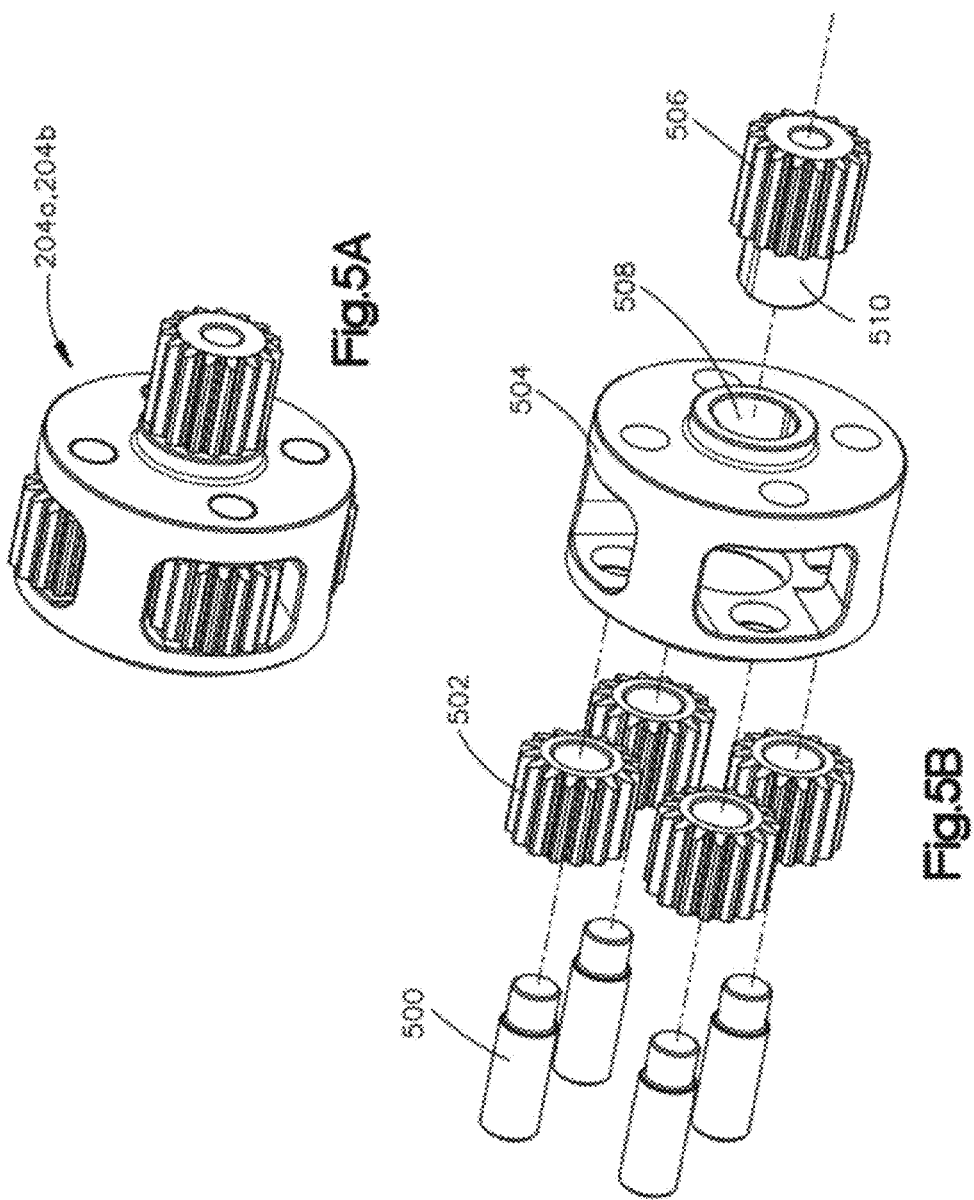

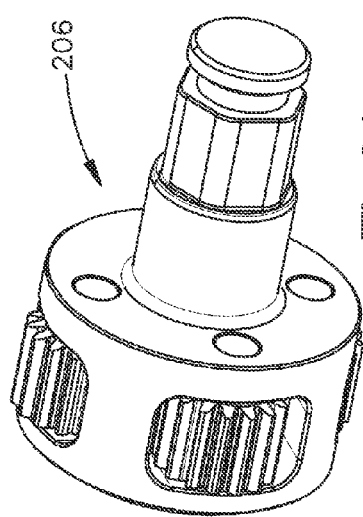
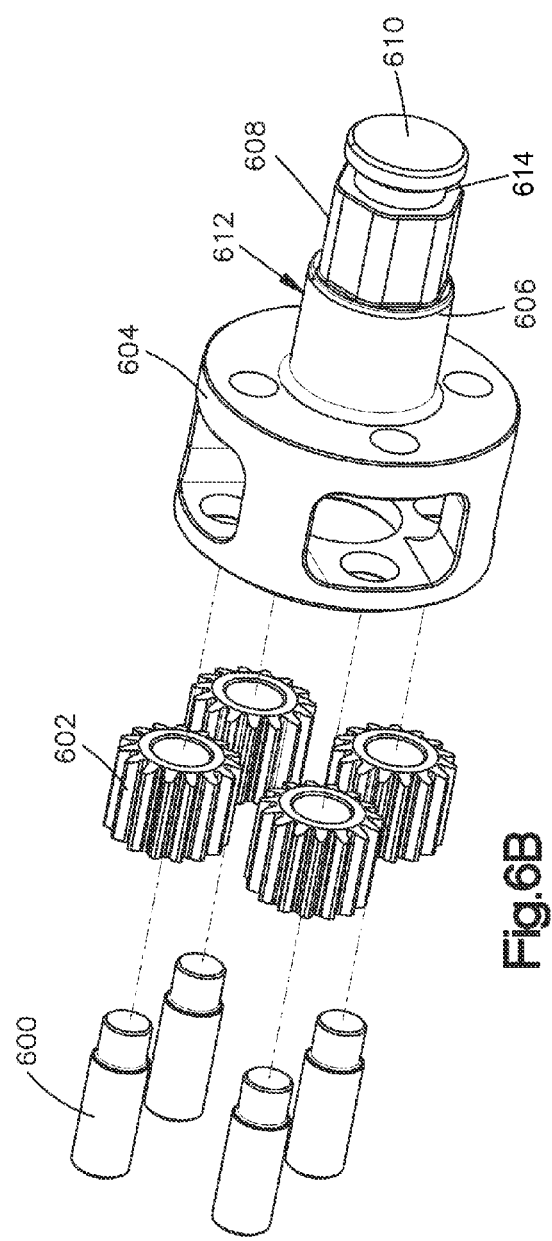
Fig.6A
Fig.6B

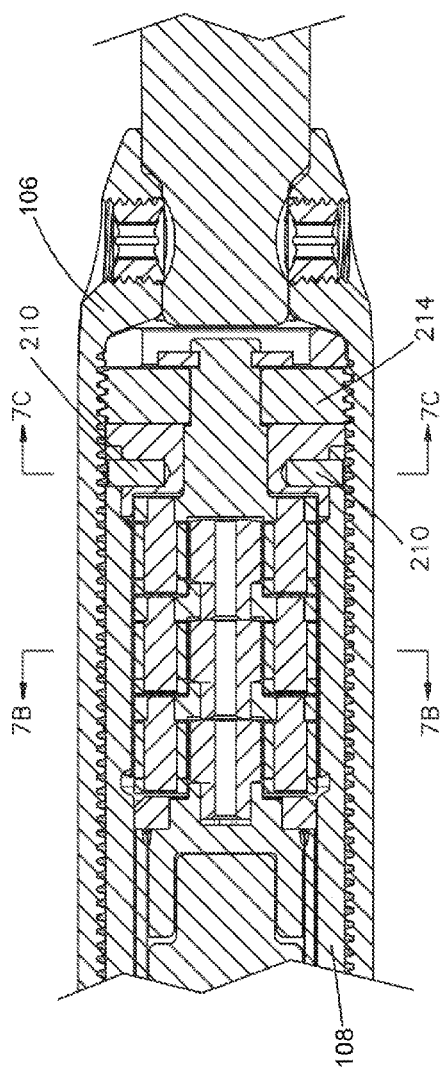
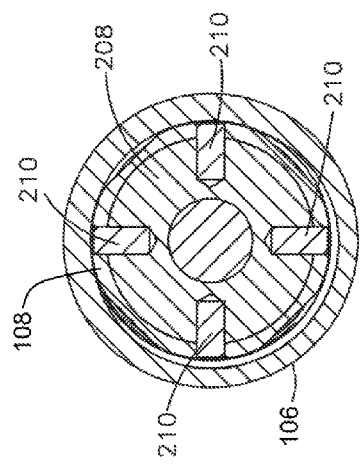
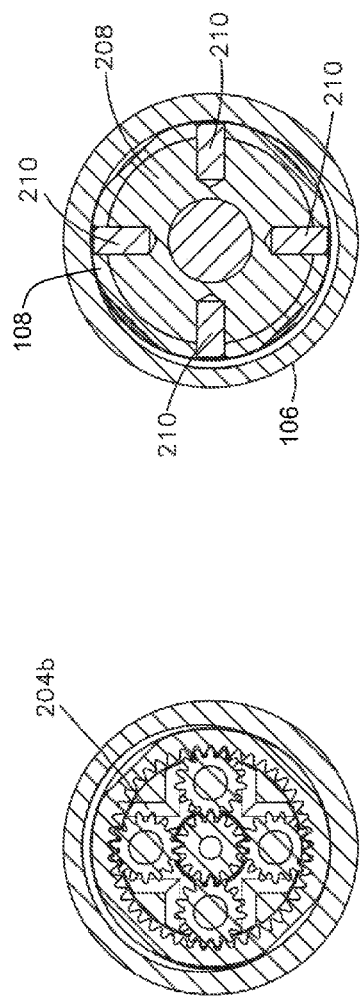

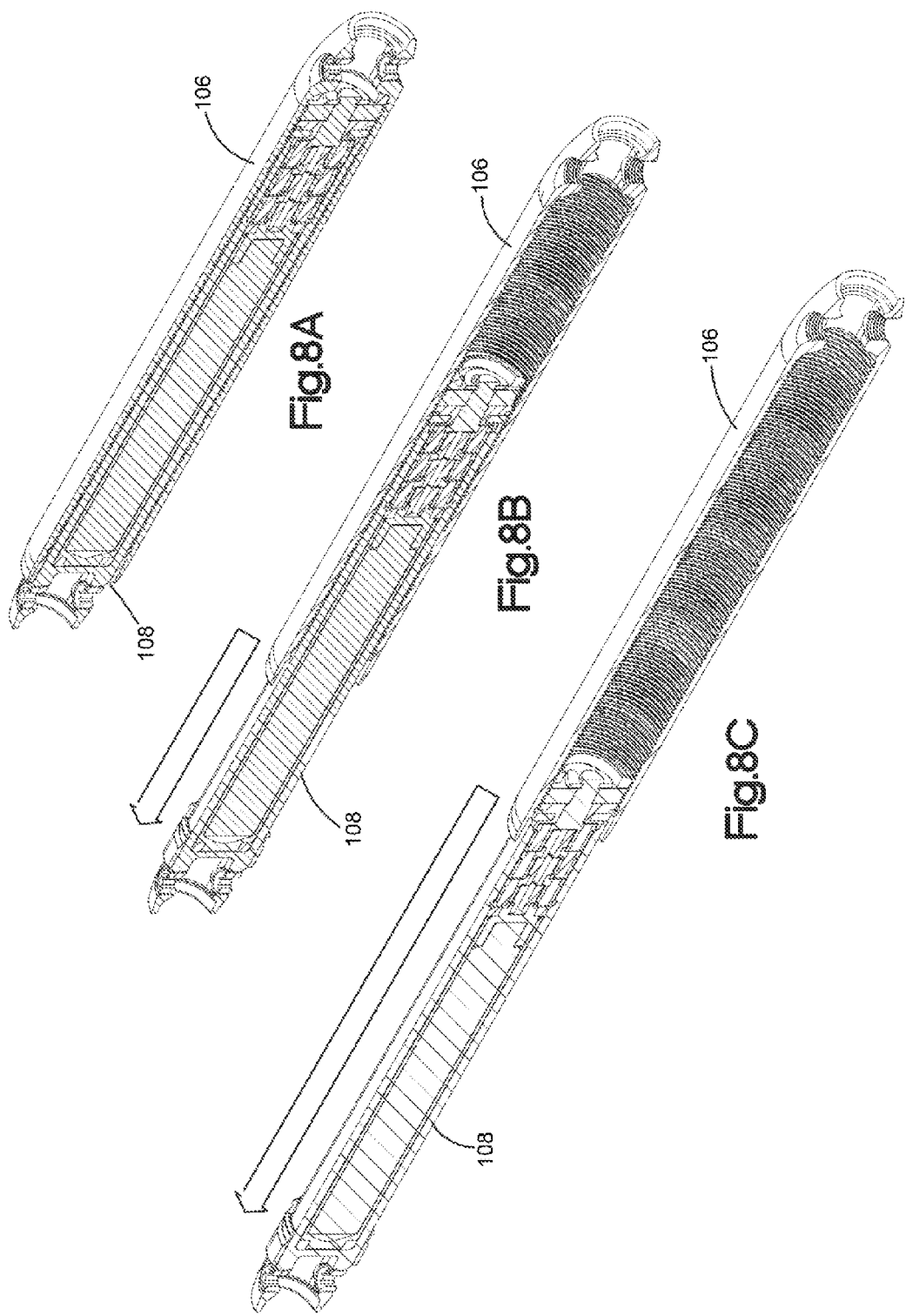

NON-FUSION SCOLIOSIS EXPANDABLE SPINAL ROD

CROSS-REFERENCE TO RELATED APPLICATION

The present disclosure claims priority to U.S. Patent Application No. 61/416,266, filed Nov. 22, 2010, entitled "Non-Fusion Scoliosis Expandable Spinal Rod," which is incorporated herein by reference in its entirety.

BACKGROUND OF THE DISCLOSURE

Scoliosis is a medical condition where an individual's spine curves off of its anatomical shape, typically in an "S" or "C" shape, and may also be rotated about a vertical axis or a longitudinal axis of the spine. Scoliosis can be a particularly painful and dangerous condition for young persons including infants, juveniles and adolescents, who are not fully grown. Young persons with scoliosis may be treated in various manners depending upon age, severity of the curve and the likelihood of progression of the condition. Conventional options for scoliosis include observation, bracing and surgery.

Surgery is typically indicated for juvenile scoliosis when there is a high likelihood of progression, the curve is causing significant pain and/or the curve is impacting physiological functions, such as breathing. Surgical intervention typically results in fusion of the impacted portion of the spine, which is ideally delayed until the patient is skeletally mature. However, certain severe cases of juvenile scoliosis require surgical intervention prior to skeletal maturity to prevent progression of the curve and/or to stabilize the spine. Multiple surgeries in such cases are common to gradually correct the curvature and/or modify the surgical construct to permit growth or to gradually move the curved or twisted spine.

SUMMARY

The present disclosure relates generally to orthopedics. More specifically, the disclosure relates to a non-fusion scoliosis construct including a magnetically actuated growing rod that permits extension of the rod, growth of the construct and extension or correction of a patient's spine without significantly invasive surgical intervention. The device includes an actively expandable rod that is mounted to a patient's spine or ribs using hooks, screws and/or other fastening mechanisms to be fixed to the posterior of the patient's spine or to nearly any other portion of the patient's spine that permits correction of an undesirable spinal curvature. The system is preferably magnetically activated from outside of the patient's body utilizing a magnetic field without further surgery for expansion.

In accordance with some implementations, there is provided a growing rod for mounting between attachment mechanisms that are secured to anatomical structures of a patient having scoliosis. The growing rod may include an outer housing, an inner housing disposed within the outer housing, and a magnet assembly rotably mounted within the inner housing. The magnet assembly may include a magnet having a first pole and a second pole. A gear reduction mechanism may be coupled to the magnet within the inner housing. The gear reduction mechanism reduces an output rotation of the magnet to rotate a driver that operates to move the inner housing along a longitudinal axis with respect to the outer housing. The growing rod may include an interchangeable first rod attached to the inner housing and an interchangeable second rod attached to the outer housing.

In accordance with some implementations, there is provided a drive mechanism for a growing rod. The drive mechanism may include an inner housing comprising a magnet assembly including a magnet having a first pole and a second pole and a gear reduction mechanism coupled to the magnet, the gear reduction mechanism reducing an output rotation of the magnet to rotate a driver. The drive mechanism may further include an outer housing coupled to the inner housing by an engagement of the driver with the outer housing and a sliding bearing that engages the outer housing and the inner housing to prevent the inner housing from spinning freely within the outer housing. Rotation of the magnet assembly causes the gear reduction mechanism to rotate the driver to cause the inner rod to move along a longitudinal axis substantially without rotation relative to the outer housing.

In accordance with yet other implementations, there is provided a growing rod that includes an outer housing and an inner housing disposed within the outer housing. The inner housing may include a magnet assembly including a magnet having a first pole and a second pole, and a gear reduction mechanism coupled to the magnet within the inner housing. A first rod is secured to the inner housing and a second rod is secured to the outer housing. The gear reduction mechanism reduces an output rotation of the magnet to rotate a driver that operates to move the inner housing along a longitudinal axis with respect to the outer housing.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE SEVERAL VIEWS OF THE DRAWINGS

The foregoing summary, as well as the following detailed description of several implementations of the device and methods of the present application, will be better understood when read in conjunction with the appended drawings. For the purposes of illustrating the growing rod or non-fusion scoliosis expandable spinal rod of the present application, there are shown in the drawings several implementations. It should be understood, however, that the application is not limited to the precise arrangements and instrumentalities shown. In the drawings:

FIG. 1A illustrates a perspective view of a growing rod or non-fusion scoliosis expandable spinal rod in accordance with the present disclosure;

FIG. 1B illustrates a cross-sectional view of growing rod or non-fusion scoliosis expandable spinal rod of FIG. 1A;

FIGS. 2A and 2B illustrate exploded views of the growing rod or non-fusion scoliosis expandable spinal rod of FIGS. 1A and 1B;

FIGS. 4A-I illustrate several views of magnetic activation of a magnet of the growing rod of FIGS. 1A and 1B;

FIGS. 5A and 5B illustrate a perspective view and exploded view, respectively, of a first stage planetary gearset;

FIGS. 6A and 6B illustrate a perspective view and exploded view, respectively, of a second stage planetary gearset;

FIGS. 7A, 7B and 7C illustrate additional details of the growing rod of FIGS. 1A and 1B; and FIGS. 8A, 8B and 8C illustrate several views of lengthening of the growing rod of FIGS. 1A and 1B.

DETAILED DESCRIPTION

Figure 2B:
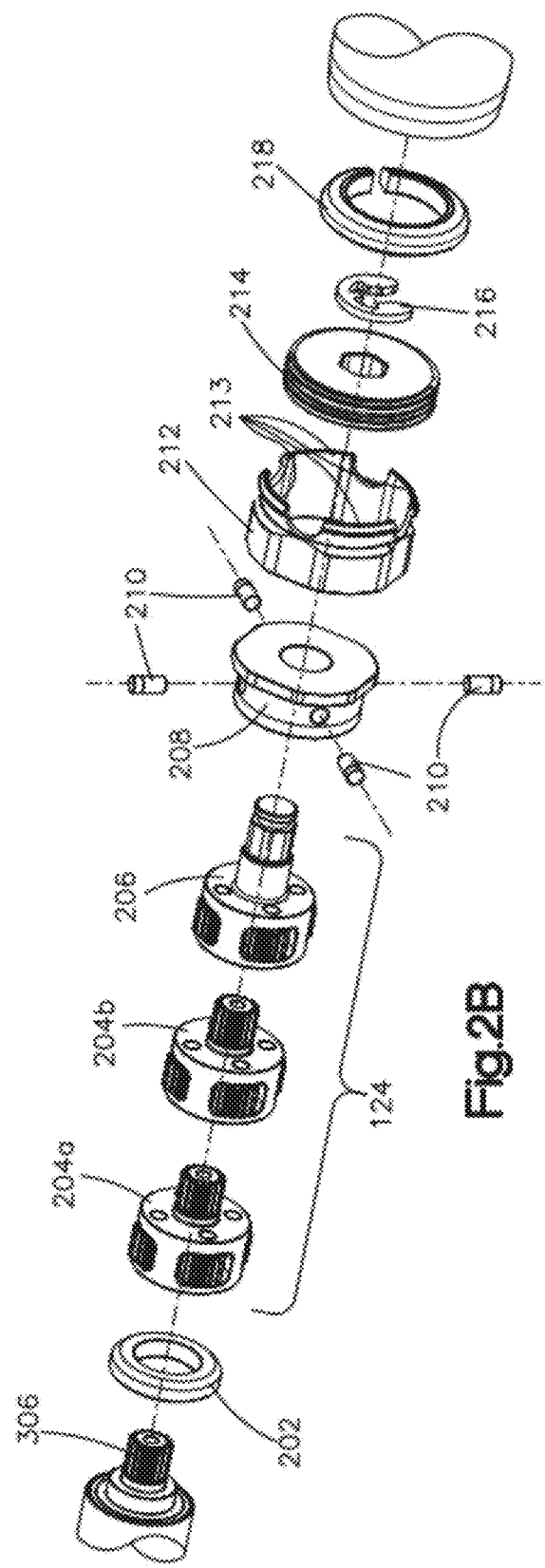

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the several implementations of the non-fusion scoliosis expandable spinal rod and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

Referring to FIGS. 1-7, a growing rod 100 in accordance with implementations of the present disclosure includes a first rod 102, an outer housing 106, an inner housing 108, and a second rod 104. A magnet assembly 300 and a gear reduction mechanism 124 are disposed within the inner housing 108. As will be described below, rotation of the magnet assembly 300 drives the gear reduction mechanism 124, which drives a threaded driver 214 within the outer housing. The rotation of the threaded driver 214 causes the inner housing to move along a longitudinal axis with respect to the outer housing, thus extending (or retracting the growing rod).

Figure 3A:
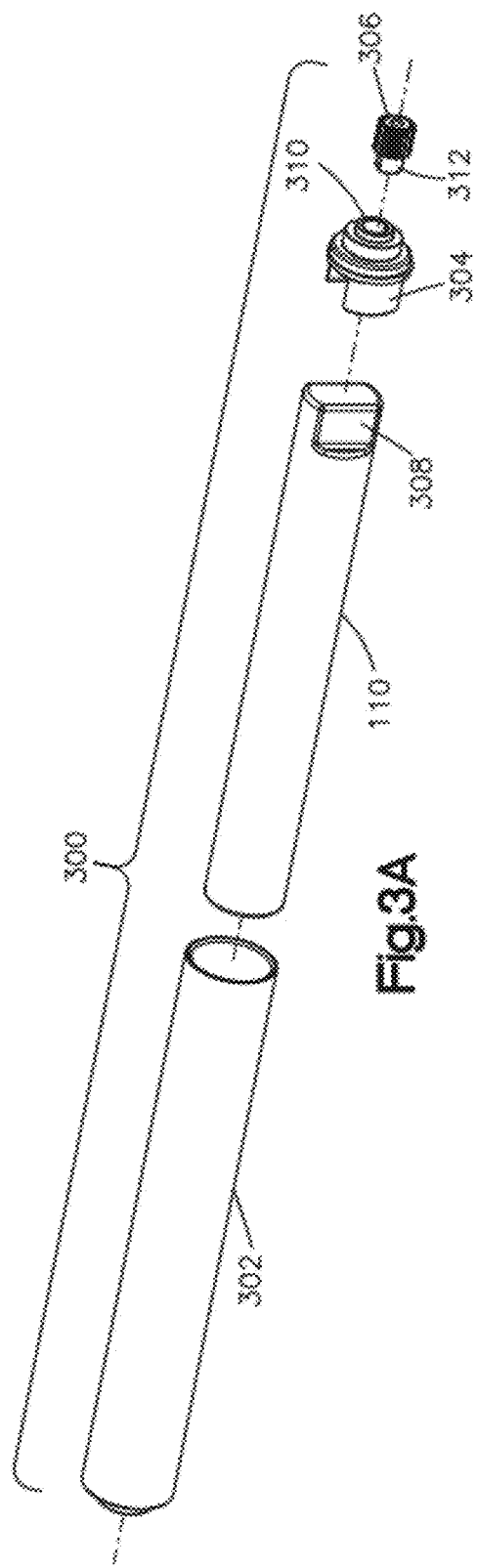
FIGS. 3A and 3B illustrate an exploded view and cross-sectional view, respectively, of a magnet assembly.
Figure 3B:
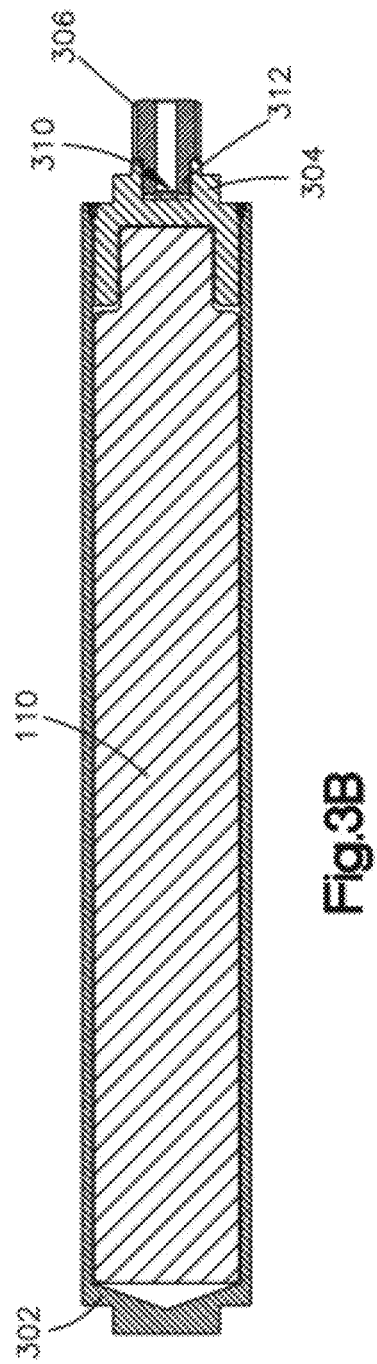

With reference to FIGS. 3A-3B, the magnet assembly 300 includes a magnet cover 302, a magnet 110, a cover lid 304 and a gear wheel 306. The magnet 110 includes a pair of opposing flats 308 that receive the cover lid 304 during assembly. The magnet 110 may be made out of Neodym and may optionally include a protective epoxy layer. The protective layer may also be made from gold or silver and have a copper or nickel under layer. To assemble the magnet assembly 300, the magnet 110 may be press fit within the magnet cover 302 and the cover lid 304 may be press fit to be received by the flats 308 to enclose the magnet cover 302. Once the cover lid 304 is positioned, it may be welded to the magnet cover 302 to seal the magnet assembly 300. The magnet assembly 300 may be sealed in such a manner in order to prevent any materials or liquid from contacting the magnet 110 and to provide for bio-compatibility. As shown, the cover lid 304 forms a keyed slot 310 into which complementary-shaped shaft portion 312 of the gear wheel 306 is received to form the complete magnet assembly 300.

The magnet 110 can be in any shape (e.g. round, square, hexagonal, octagonal etc.) so long as it fits within the magnet cover 302. As shown in FIGS. 4A-I, the magnet 110 can be formed having a hollowed center with diametric poles, can be massive with diametric poles, can have multiple diametrical poles, etc. As shown, by applying a magnetic field from an external magnet, the magnet 110 will be urged to rotate in a predetermined direction.

As shown in FIGS. 1, 2, 5 and 6, the gear reduction mechanism 124 is provided within the inner housing 108. The gear reduction mechanism 124 includes at least a two stage assembly of planetary gearsets. It is noted that other gear arrangements may be used, and planetary gearsets are shown as an exemplary implementation. A first stage 204A/204B is shown in FIGS. 2B, 5A and 5B. The first stage 204A/204B includes a carrier 504 that receives, e.g., four (or other number) planet gears 502 that each rotate on a mount 500 that is press fit into the carrier 504. A sun gear 506, having a slotted shaft 510, is received within a complementary slotted recess 508 formed in face the carrier. The first stage 204A/204B may be used as an input to the gear reduction mechanism 124.

In some implementations, such as shown in FIG. 2B, more than one first stage 204A/204B may be included in the gear reduction mechanism 124 to achieve a desire reduction. In some implementations, the first stage is designed such that a plurality of first stages may be connected in series. In such an arrangement, as shown in FIG. 7B, the planet gears of a subsequent first stage is driven by the sun gear of a preceding first stage.

As shown in FIGS. 2B and 6A and 6B, a second stage 206 includes a carrier 604 that receives, e.g., four (or other number) planet 602 gears that each rotate on a mount 600 that is press fit into the carrier 604. The number of gears in the second stage 206 is the same as the number provided in the first stage 204A/204B. The face of the carrier 604 in the second stage 206 includes a catch 612. The catch 612 has a round base 606, a midsection 608 having hexagonal cross-section and a circular upper section 610 separated from the midsection 608 by an annular recess 614. The second stage 206 may be used as an output of the gear reduction mechanism 124.

Thus, the assembled gear reduction mechanism 124 may include, e.g., three stages. However, any number of sections may be provided in order to achieve a desired input reduction. For example, each stage may provide a 4× gear reduction. As such, the total reduction may be determined in accordance with the number of stages provided in the gear reduction mechanism 124. The gear ratios may be changed according to the following relationship in Table 1:

TABLE 1

| Gear ratio | Modulus | Gear ratio total | Thread pitch | Turns for 1 mm |
|---|---|---|---|---|
| i | m | $i^3$ | P | x |
| [—] | [—] | [—] | [mm] | [—] |
| 3.0 | 0.15 | 64.0 | 0.5 | 128.0 |

In accordance with the above, the gear reduction mechanism 124 may be configured such that 128 turns of gear reduction mechanism 124 extends or retracts the growing rod 100 by 1 mm. Other ratios may be used to control the rate at which the gear reduction mechanism 124 drives the growing rod 100. Optionally or additionally, sizes of the gears within the stages may be different. For example, the stages closer to the input may be smaller, where the gears near the output are relatively larger.

To assemble the inner housing 108, an inner bearing 201 is placed within the interior space of the inner housing 108. The magnet assembly 300 is then pressed into the inner housing 108 such that a far end of the magnet assembly 300 is received within the inner bearing 201. An outer bearing 202 is then placed in the inner housing 108 such that it is received by the cover lid 304 of the magnet assembly 300. Next the first stage(s) 204A/204B are inserted such that an inner first stage receives the gear wheel 306 of the magnet assembly 300. The gear wheel 306 of the magnet assembly 300 is a rotational input to drive the gear reduction mechanism 124. As noted above, one or more first stages may be placed into the inner housing 108 as part of the gear reduction mechanism 124, followed by a second stage 206 as an output. The assembly of the inner housing 108 is completed by placing a bearing shoulder 208 into the inner housing 108 that is, e.g., secured to the drive housing by pins 210. As shown, four pins may be used to secure the bearing shoulder 208 to the inner housing 108, but other numbers of pins may be used. The catch 612 of the second stage 206 protrudes through the bearing shoulder 208. As a result, the magnet assembly 300 and gear reduction mechanism 124 are able to rotate freely within the inner housing 108.

With reference to FIGS. 1B and 2A, to engage the inner housing 108 with the outer housing 106, a bearing 212 is slide fit around the outer circumference of the inner housing 108 at a far end. An inner surface of bearing 212 mates with a ribbed outer surface of the inner housing 108 to prevent rotation of the bearing 212 around the circumference of the inner housing 108. A threaded driver 214 having a hexagonally-shaped center hole is received and mounted to the catch 612 and secured thereto by a snap-fit locking clip 216. An insert 218 is placed within the outer housing 106 to act as a stop.

To assemble the growing rod 100, the outer housing 106 is placed over the inner housing 108 and rotated to threadedly retract the inner housing 108 into the outer housing 106 by cooperation of an inner threaded surface of the outer housing 108 and the threaded driver 214. The inner housing 108 is retracted into the outer housing 106 until reaching the insert 218. As the inner housing 108 is retracted, flats 213 provided in the bearing 212 snap fit to an inner surface of the outer housing 106 to complete the assembly. Four flats may be provided with the bearing 212. The flats serve to secure the far end of the outer housing 106 to the inner housing 108 and to counteract the moment produced by the inner housing 108 as it rotates. Thus, the flats 213 prevent the inner housing 108 from spinning freely within the outer housing 106.

Referring now to FIGS. 1B and 2A, the first rod 102 is secured to the inner housing 108 by the threaded pins 222A/222B that engage a circumferential recess 116. A rounded end 118 of the first rod 102 has at least one flat surface that is received by a complementary flat surface within the inner housing 108 to prevent rotation of the first rod 102 with respect to the inner housing 108. In some implementations, the threaded pins 222A/222B are inserted into threaded holes 220 of the inner housing 108 from the inside of the inner housing 108. Each threaded pin 222A or 222B includes a locking surface that engages a ledge of a respective threaded hole 220 to prevent the threaded pin from falling out of the inner housing 108. The threaded pins 222A/222B may be screwed from the outside using an appropriate tool to secure the first rod 102 within the inner housing 108.

The second rod 104 is secured to the outer housing 106 by the threaded pins 226A/226B that engage a circumferential recess 120. A rounded end 122 of the second rod 104 has at least one flat surface that is received by a complementary flat surface within the outer housing 106 to prevent rotation of the second rod 104 with respect to the outer housing 106. Similar to the inner housing, the threaded pins 226A/226B used in the outer housing 106 may be inserted into the threaded 224 holes from the inside. Each threaded pin 226A or 226B may include a locking surface that engages a ledge of a respective threaded hole to prevent the threaded pin from falling out of the outer housing 106. The treaded pins 226A/226B may be screwed from the outside using an appropriate tool to secure the second rod 104 within the outer housing 106.

Thus, in view of the assembly noted above the completed, assembled growing rod 100 may be exemplified by that illustrated in FIGS. 1A and 1B. The growing rod and its components may be constructed of titanium or titanium alloys but are not so limited and may be constructed of cobalt chromium material, polymeric materials or nearly any bio-compatible material. Such materials should be relatively strong and stiff, able to take on the general size of the growing rod and its components and able to withstand normal operating conditions of the growing rod. The bearings and the insert may be constructed of a Polyether ether ketone (PEEK) material that is biocompatible and has a relatively low coefficient of friction. The bearings are not limited to constructions utilizing PEEK materials and may be constructed of nearly any material that permits the associated parts to rotate (e.g., ball bearings). The outer housing 106 and the inner housing 108 may be made from any material that does not exhibit magnetic properties, in order to allow the magnetic field of the external magnet to pass there through to affect the magnet 110 within the growing rod.

In some implementations, the outer surface of the growing rod 100 may be polished to substantially remove any rough surfaces to reduce the likelihood that the body will attach to the growing rod. A coating may be placed on the growing rod for a similar purpose. In yet other implementations, the magnet assembly 300 may be replaced by an electric motor that rotationally drives the gear reduction mechanism 124.

To actuate the growing rod 100 to expand within, e.g., a patient undergoing treatment, an external magnet may be used as a source of a magnetic field to cause rotation of the magnet 110. As show in FIG. 8, the growing rod initially have a contracted length. Upon excitation by the external magnetic field, the magnet assembly 300 drives the gear reduction mechanism 124 to rotate the threaded driver 214. As the threaded driver 214 rotates, the inner housing is driven outwardly by cooperation of the threaded driver 214 and the inner threaded surface of the outer housing 106 to laterally drive the inner housing 108 with respect to the outer housing 106.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the present description.

What is claimed:

1. A growing rod, comprising:
   an outer housing;
   an inner housing disposed within the outer housing;
   a magnet assembly rotably mounted within the inner housing, the magnet assembly including a magnet having a first pole and a second pole;
   a gear reduction mechanism coupled to the magnet within the inner housing, the gear reduction mechanism reducing an output rotation of the magnet to rotate a threaded driver that operates to move the inner housing along a longitudinal axis with respect to the outer housing;
   a first rod attached to the inner housing; and
   a second rod attached to the outer housing,
   wherein the inner housing further includes:
      an inner bearing that is disposed within an interior space of the inner housing, the inner bearing receiving the magnet;
      an outer bearing that is received by a cover lid of the magnet assembly;
      the gear reduction mechanism; and
      a bearing shoulder secured to the inner housing to retain the magnet assembly and the gear reduction mechanism within the inner housing such that the magnet assembly and the gear reduction mechanism rotate freely within the inner housing, the bearing shoulder secured to the inner housing by a pin, the bearing shoulder including a ledge extending around the perimeter of the bearing shoulder sized and configured to contact an end of the inner housing.

2. The growing rod of claim 1, wherein the first rod moves along the longitudinal axis substantially without rotation relative to the first rod.

3. The growing rod of claim 1, the gear reduction mechanism further comprising:
   a first stage comprising a planetary gearset; and
   a second stage comprising a planetary gearset that receives the first stage, the second stage being an output of the gear reduction mechanism.

4. The growing rod of claim 3, the magnet assembly further comprising a gear wheel,
   wherein the gear wheel is received by the first stage to drive the gear reduction mechanism upon rotation of the magnet assembly.

5. The growing rod of claim 4, the second stage includes a catch extending from the gear reduction mechanism, wherein the catch rotates approximately one-sixty-fourth of a rotation for each full rotation of the gear wheel.

6. The growing rod of claim 4, wherein rotation of the gear wheel is transmitted by the gear reduction mechanism to rotate the threaded driver.

7. The growing rod of claim 1, wherein the outer housing and the inner housing are a non-magnetizable material.

8. The growing rod of claim 7, wherein the non-magnetizable material comprise one of titanium, a titanium alloy material, a cobalt-chromium material and a polymeric material.

9. The growing rod of claim 1, wherein the inner housing is moved relative to the outer housing by passing a magnetic field in proximity to the growing rod to cause the magnet to rotate about a longitudinal axis of the growing rod.

10. The growing rod of claim 1, further comprising a bearing that is slide fit around an outer circumference of the inner housing,
    wherein an inner surface of bearing mates with a ribbed outer surface of the inner housing, and
    wherein the bearing includes a plurality of flats that snap fit to an inner surface of the outer housing.

11. The growing rod of claim 10, wherein the plurality of flats prevent the inner housing from spinning freely within the outer housing.

12. The growing rod of claim 1, wherein the magnet assembly includes a magnet cover that receives the magnet, and
    wherein the magnet includes opposing flats to which a cover lid is received to enclose the magnet cover.

13. The growing rod of claim 12, wherein the cover lid is laser welded to the magnet cover to seal the magnet assembly.

14. The growing rod of claim 12, wherein the cover lid receives a gear wheel that drives the gear reduction mechanism.

15. The growing rod of claim 1, wherein the magnet includes diametric poles.

16. The growing rod of claim 1, wherein the first rod is secured to the inner housing by threaded pins that engage a circumferential recess of the first rod, and
    wherein a rounded end of the first rod has at least one flat surface that is received by a complementary flat surface within the inner housing to prevent rotation of the first rod with respect to the inner housing.

17. The growing rod of claim 16, wherein the threaded pins engage the inner housing from an inside of the inner housing, and
    wherein the threaded pins are stopped from the inside of the inner housing from falling out of the inner housing.

18. The growing rod of claim 1, wherein the second rod is secured to the outer housing by threaded pins that engage a circumferential recess of the second rod, and
    wherein a rounded end of the second rod has at least one flat surface that is received by a complementary flat surface within the outer housing to prevent rotation of the second rod with respect to the outer housing.

19. The growing rod of claim 18, wherein the threaded pins engage the outer housing from an inside of the outer housing, and
    wherein the threaded pins are stopped from the inside of the outer housing from falling out of the outer housing.

20. The growing rod of claim 1, wherein the outer housing and the inner housing are a non-magnetizable material.

21. A drive mechanism for a growing rod, comprising:
    an inner housing comprising a magnet assembly including a magnet having a first pole and a second pole and a gear reduction mechanism coupled to the magnet, the gear reduction mechanism reducing an output rotation of the magnet to rotate a driver; and
    an outer housing coupled to the inner housing by an engagement of the driver with the outer housing and a bearing that engages the outer housing and the inner housing to prevent the inner housing from spinning freely within the outer housing,
    wherein the inner housing further includes:
      an inner bearing that is disposed within an interior space of the inner housing, the inner bearing receiving the magnet;
      an outer bearing that it is received by the magnet assembly; and
      a bearing shoulder secured to the inner housing to retain the magnet assembly and the gear reduction mechanism within the inner housing such that the magnet assembly and gear reduction mechanism rotate freely within the inner housing,
    wherein rotation of the magnet assembly causes the gear reduction mechanism to rotate the driver to cause the inner rod to move along a longitudinal axis substantially without rotation relative to the outer housing.

22. The drive mechanism of claim 21, the gear reduction mechanism further comprising:
    a first stage comprising a planetary gearset; and
    a second stage comprising a planetary gearset that receives the first stage, the second stage being an output of the gear reduction mechanism.

23. The drive mechanism of claim 22, the magnet assembly further comprising a gear wheel, wherein the gear wheel is received by the first stage to drive the gear reduction mechanism upon rotation of the magnet assembly.

24. The drive mechanism of claim 21, wherein rotation of the magnet assembly by an external magnetic field causes magnet assembly to drive the gear reduction mechanism.

25. The drive mechanism of claim 24, wherein the outer housing and the inner housing are a non-magnetizable material.

26. A growing rod, comprising:
    an outer housing;
    an inner housing disposed within the outer housing, the inner housing including a magnet assembly including a magnet having a first pole and a second pole, and a gear reduction mechanism coupled to the magnet within the inner housing;
    a first rod is secured to the inner housing by threaded pins and a rounded end having at least one flat surface that is received by a complementary flat surface within the inner housing to prevent rotation of the first rod with respect to the inner housing; and
    a second rod is secured to the outer housing by threaded pins and wherein a rounded end having at least one flat surface that is received by a complementary flat surface within the outer housing to prevent rotation of the second rod with respect to the outer housing,
wherein the inner housing further includes:
- an inner bearing that is disposed within an interior space of the inner housing, the inner bearing receiving the magnet;
- an outer bearing that is received by a cover lid of the magnet assembly;
- the gear reduction mechanism and
- a bearing shoulder secured to the inner housing to retain the magnet assembly and the gear reduction mechanism within the inner housing such that the magnet assembly and gear reduction mechanism rotate freely within the inner housing, wherein the gear reduction mechanism reduces an output rotation of the magnet to rotate a driver that operates to move the inner housing along a longitudinal axis with respect to the outer housing.

27. The growing rod of claim 26, the gear reduction mechanism further comprising:
- a first stage comprising a planetary gearset; and
- a second stage comprising a planetary gearset that receives the first stage, the second stage being an output of the gear reduction mechanism.

28. The growing rod of claim 26, the gear reduction mechanism being driven by rotation of a gear wheel of the magnet assembly,
wherein the gear reduction mechanism rotates a threaded driver that engages an inner threaded surface of the outer housing to drive the inner housing along the longitudinal axis with respect to the outer housing.

29. The growing rod of claim 26, wherein the inner housing is moved relative to the outer housing by passing a magnetic field in proximity to the growing rod to cause the magnet to rotate about a longitudinal axis of the growing rod.

30. The growing rod of claim 29, wherein the outer housing and the inner housing are a non-magnetizable material.

* * * * *